United States Patent [19]

Saito et al.

[11] 4,437,992
[45] Mar. 20, 1984

[54] PROCESS FOR CONTROLLING AN AERATION TANK IN AN ACTIVATED SLUDGE SEWAGE TREATMENT

[75] Inventors: Yukio Saito; Shunsuke Nogita; Syoji Watanabe; Kenji Baba, all of Hitachi, Japan

[73] Assignee: Hitachi, Ltd., Tokyo, Japan

[21] Appl. No.: 355,110

[22] Filed: Mar. 5, 1982

Related U.S. Application Data

[63] Continuation of Ser. No. 149,995, May 15, 1980, abandoned.

[30] Foreign Application Priority Data

May 16, 1979 [JP] Japan .................................. 54-59153

[51] Int. Cl.³ .................................................. C02F 3/12
[52] U.S. Cl. ..................................... 210/603; 210/614; 210/626; 210/96.1
[58] Field of Search ................ 210/603, 604, 614, 626, 210/627, 628, 96.1, 903, 739, 218; 73/19; 422/79; 435/807, 39

[56] References Cited

U.S. PATENT DOCUMENTS

| 3,740,320 | 6/1973 | Arthur | 435/807 |
| 4,071,443 | 1/1978 | Gorski et al. | 210/604 |
| 4,130,481 | 12/1978 | Chase et al. | 210/614 |
| 4,183,810 | 1/1980 | Baenens et al. | 210/614 |

FOREIGN PATENT DOCUMENTS

| 54-118292 | 9/1979 | Japan | 210/614 |
| 55-134700 | 10/1980 | Japan | 210/614 |
| 581087 | 12/1977 | U.S.S.R. | 210/96.1 |

*Primary Examiner*—Benoit Castel
*Attorney, Agent, or Firm*—Antonelli, Terry & Wands

[57] ABSTRACT

It is necessary for maintaining a good assimilating characteristic of microorganisms upon organic matter in an aeration tank to control a gas flow rate and a return sludge flow rate to optimum values. To this effect, it is necessary to know a concentration of organic matter or a organic load. In the present invention, it is confirmed that carbon dioxide ($CO_2$) or nitrous oxide ($N_2O$) in an exhaust gas from the aeration tank has a correlation with it, and the aeration tank is controlled as $N_2O$ or $CO_2$ as an index. Furthermore, it is confirmed that $CO_2$ formation rate has a good correlation with COD or BOD in the upstream half section of the aeration tank, whereas $N_2O$ formation rate has a good correlation with COD or BOD in the latter half section thereof along sewage flow direction, and more improved control can be attained by a combination of both $CO_2$ and $N_2O$ indices.

7 Claims, 21 Drawing Figures

FIG. 18
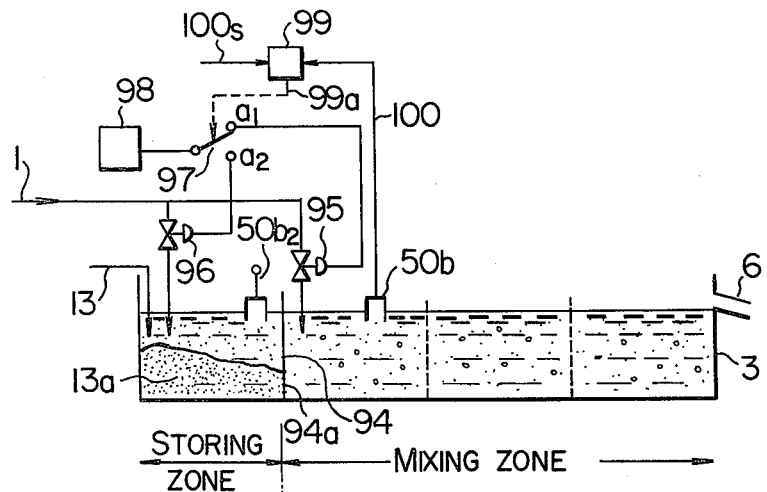
(a)
(b)
(c)
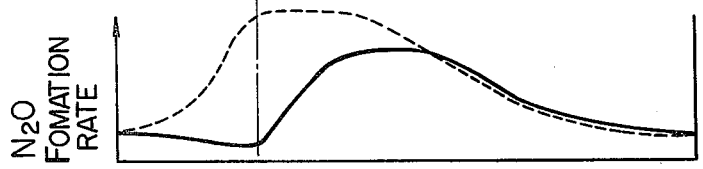
(d)

FIG. 19
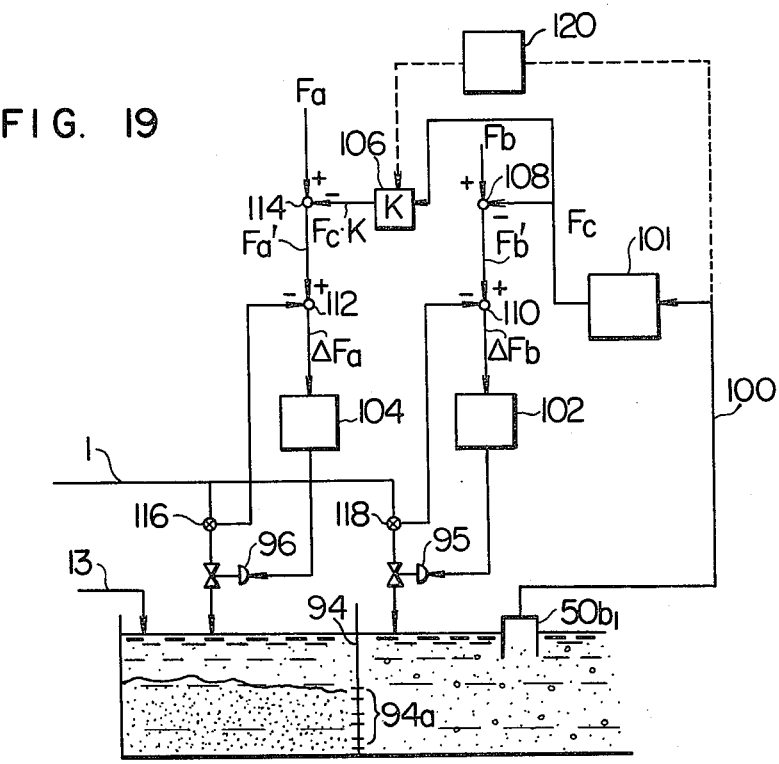
FIG. 21
(a)
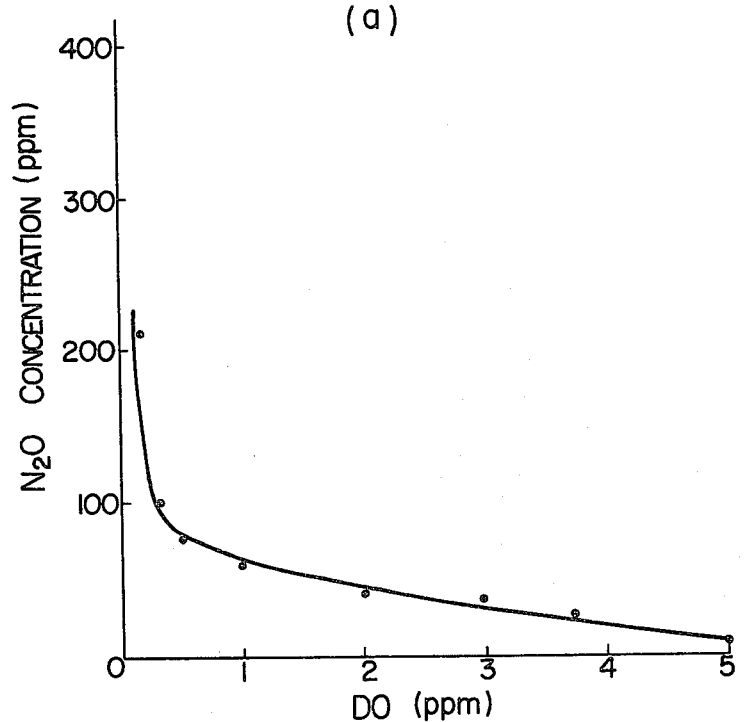
(b)
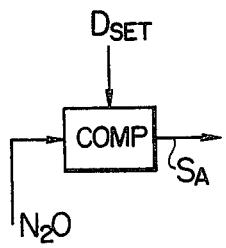

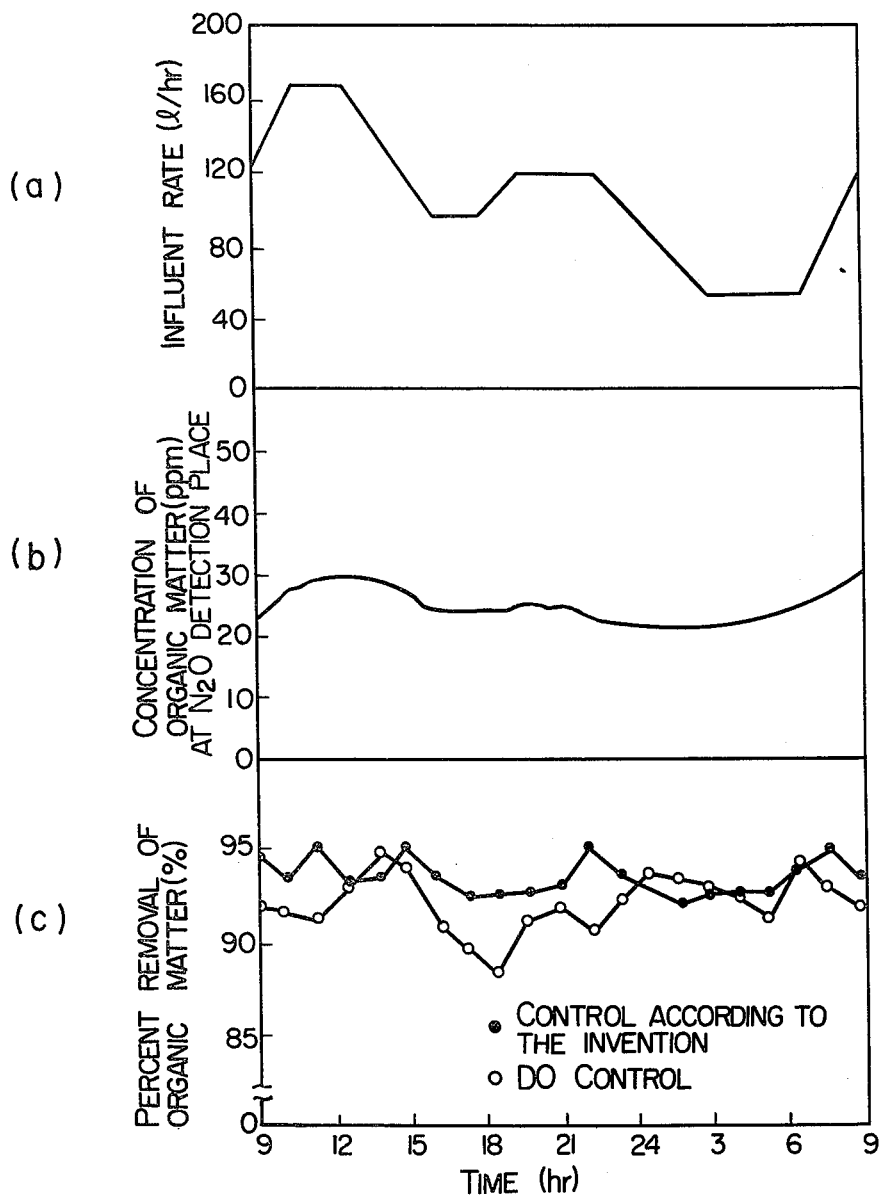

PROCESS FOR CONTROLLING AN AERATION TANK IN AN ACTIVATED SLUDGE SEWAGE TREATMENT

This is a continuation of application Ser. No. 149,995, filed May 15, 1980, now abandoned.

BACKGROUND OF THE INVENTION

1. Field of the Invention

This invention relates to a process for controlling an aeration tank in an apparatus for sewage treatment by activated sludge.

The apparatus for sewage treatment by activated sludge is widely used for removing organic matter in municipal sewage and industrial waste water. The sewage treatment by activated sludge is a process for converting the organic matter in the sewage to sludge by an assimilating action for a group of microorganisms called activated sludge by blowing an oxygen-containing gas, for example, air into an aeration tank, thereby supplying oxygen thereto. The aerated sewage is led to a sedimentation tank from the aeration tank to concentrate and separate the sludge from water, and the concentrated sludge is returned to the aeration tank, or withdrawn to the outside of the apparatus as excess sludge, whereas supernatant water is discharged as treated effluent water.

One of the most important problems in such an apparatus for sewage treatment as described above is control of the aeration tank, that is, control of flow rate of sludge and flow rate of oxygen to the most suitable state for promoting the assimilating action of the microorganisms in the aeration tank.

The present invention concerns a process for controlling an aeration tank by detecting a concentration of nitrous oxide ($N_2O$) or carbon dioxide ($CO_2$) in an exhaust gas from the aeration tank, controlling the activation state of the aeration tank on the basis of the detected concentration, and maintaining the aeration tank in a suitable state for the assimilating action of the microorganisms therein.

2. Description of the Prior Art

In order to efficiently carry out sewage treatment by activated sludge, it is necessary:

(1) to convert the organic matter in the sewage to activated sludge as much as possible, and
(2) to maintain activated sludge with good settling characteristic, and make the activated sludge fully settlable in the sedimentation tank, thereby making the treated water (effluent water) free from the organic matter.

In order to meet the requirement (1), it is preferable to detect a concentration of organic matter in sewage and that in treated water. Generally, a concentration of organic matter is represented and measured by chemical analysis or by a total organic carbon meter (total organic carbon will be hereinafter referred to as TOC). However, the chemical analysis is based on a manual procedure, and requires much time in measurement, and thus it is difficult to utilize the chemical analysis in controlling an aeration tank. The TOC meter determines a concentration of organic matter in sewage, and also requires several ten minutes for the measurement, and thus it is difficult to utilize it in on-line control.

In order to meet the requirement (2), it is necessary to maintain the ratio of organic matter to the unit amount of sludge, that is, a load of organic matter, at an appropriate value, but this ultimately leads to the detection of a concentration of organic matter in sewage.

On the other hand, the art of controlling an aeration tank is disclosed in U.S. Pat. No. 3,684,702 entitled "method and apparatus for determining the biochemical decomposability of sewage", which relates to optimum control of biological decomposition in an aeration tank by measuring a biochemical oxygen demand (BOD) of sewage and controlling return sludge flow rate.

A case of a digestor, though quite different from the subject matter of the present invention as will be briefly mentioned below, by indirectly measuring the state of the tank, and controlling the tank, is disclosed in U.S. Pat. No. 4,062,770 entitled "Method of and apparatus for digesting organic waste and/or sewage sludge", whose subject matter is a process for organic solid waste or sewage sludge (solid matter), that is, a digestor, and is quite different from the activated sludge process as in the present invention. The digestor is based on dissimilation or sludge decomposition, whereas the activated sludge process is based on assimilation or cell synthesis to convert the soluble organic matter in sewage to activated sludge.

BRIEF SUMMARY OF THE INVENTION

The main object of the present invention is to provide a novel controlling process for suitable control of an aeration tank in an apparatus for sewage treatment by activated sludge.

Another object of the present invention is to control an aeration tank by estimating an operating state of the aeration tank from a specific component in an exhaust gas from the aeration tank.

The present invention is characterized by estimating an organic load or a concentration of organic matter in an aeration tank from a concentration of carbon dioxide $CO_2$ or nitrous oxide ($N_2O$) in an exhaust gas from the aeration tank, thereby controlling an air flow rate or a return sludge flow rate to the aeration tank.

The present invention is further characterized by measuring a concentration of $CO_2$ at the sewage influent side (upstream side) of an aeration tank and a concentration of $N_2O$ at the effluent side (downstream side) thereof, and controlling an air flow rate or a return sludge flow rate to the aeration tank according to both values of measured concentrations.

The present invention is still further characterized by correcting the detected concentrations of $CO_2$ and $N_2O$ in an exhaust gas from an aeration tank by an influent sewage flow rate, and controlling an air flow rate or a return sludge flow rate to the aeration tank in accordance with the corrected concentrations of $CO_2$ and $N_2O$.

BRIEF DESCRIPTION OF THE DRAWINGS

FIGS. 18, and 19 are diagrams showing one example of an aeration tank having a dynamic sludge storing zone according to other embodiments of the present invention.

FIG. 20 shows comparison between the present invention and the conventional dissolved oxygen (DO) control art.

FIG. 21 shows relationships between DO and $N_2O$ concentration.

DESCRIPTION OF THE PREFERRED EMBODIMENTS

Figure 1:
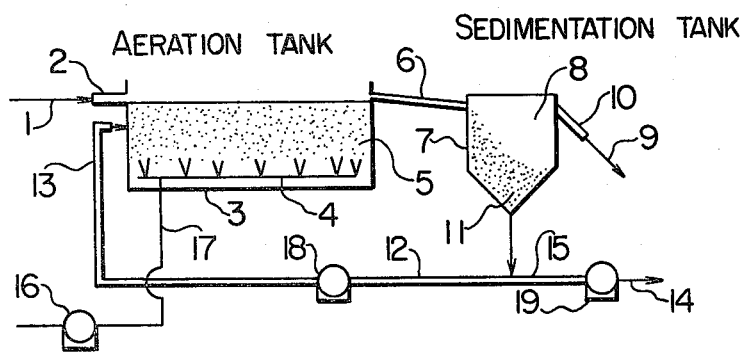
FIG. 1 is a schematic flow diagram of an apparatus for sewage treatment by activated sludge.

In FIG. 1, a schematic flow diagram of an apparatus for sewage treatment by activated sludge is shown.

In an aeration tank 3, influent sewage 1 is mixed with return sludge 13 from a sedimentation tank 7, stirred by air 17 supplied by a blower 16, and supplied with oxygen from the air. Organic matter in the influent sewage 1 is converted to sludge in the aeration tank 3 by assimilating action of microorganisms. The effluent water 6 from the aeration tank 3 is led to the sedimentation tank 7. In the sedimentation tank 7, supernatant water 8 is separated from sludge precipitate 11 by settling, and the supernatant water 8 is discharged therefrom as treated water 9. Most of the sludge precipitate in the sedimentation tank 7 is withdrawn by a return sludge pump 18 and returned to the aeration tank 3. The remaining portion of the sludge is taken to the outside of the system by a discharge sludge pump 19.

Numeral 12 designates a conduit to the return sludge pump 18, numeral 15 a conduit to the discharge sludge pump 19, and numeral 10 a discharge conduit from the sedimentation tank 7.

In order to efficiently carry out sewage treatment in such a process for sewage treatment by activated sludge as outlined above, it is necessary to convert the organic matter in the sewage to activated sludge as much as possible in the aeration tank 3 and to make the activated sludge fully settle in the sedimentation tank 7 to prevent it from discharging in the treated water. It has been experimentally clarified that an organic load is an important index for simultaneously satisfying the aforementioned two conditions. The organic load is the weight of organic matter in influent sewage per unit weight of activated sludge in an aeration tank. In order to control the organic load as an operating index, it is however necessary to use an organic matter analyzer for sewage that can work continuously for a long period, but a satisfactory organic matter analyzer for such a duty is not available.

Thus, attempts have been so far made to adjust a return sludge rate with a view to maintaining the organic load to an appropriate value in view of the past tendency in changes as to water quality index such as BOD or COD (chemical oxygen demand) of influent sewage. However, it is difficult to detect the organic load on line, when the organic load based on BOD and COD is used as the operating index, and thus an improvement of water quality has been so far unexpected as a disadvantage.

Under these situations, the present invention has been established by estimating a concentration of organic matter in an aeration tank from a specific component in an exhaust gas from the aeration tank, and controlling water quality without using such a water quality analyzer as mentioned above.

Figure 2:
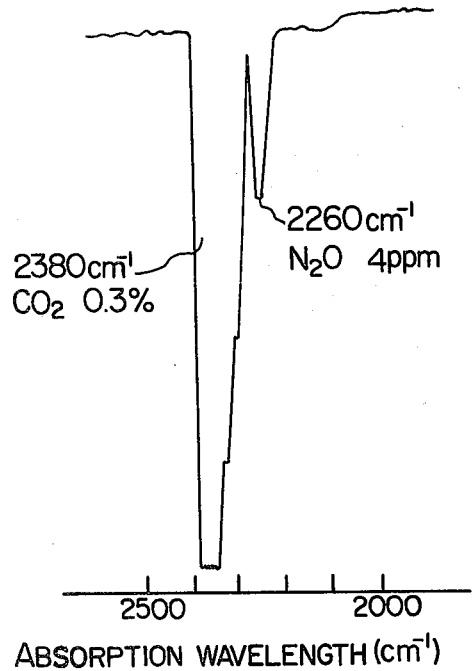
FIG. 2 is a diagram showing one example of absorption characteristic by an infrared gas analyzer.

In FIG. 2, one example of analytical results of an exhaust gas from an aeration tank according to a highly sensitive infrared gas analyzer is shown, where it is shown that $CO_2$ is detected at the wavelength of 2,380 $cm^{-1}$ and $N_2O$ at the wavelength of 2,260 $cm^{-1}$. It has been so far presumed that $N_2O$ is not substantially formed under the aerobic conditions as in an aeration tank, but it has been confirmed by the inventors that $N_2O$ is formed even under the aerobic conditions, though in a very small amount.

Figure 3:
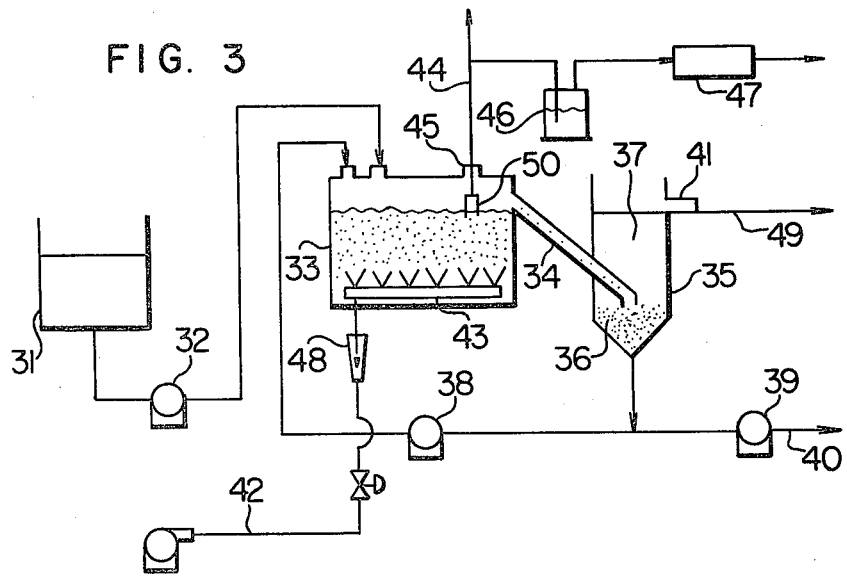
FIG. 3 is a schematic flow diagram of a test apparatus for sewage treatment by activated sludge.

In FIG. 3, a test apparatus used for determining relationships between the $N_2O$ concentration of an exhaust gas from an aeration tank and other factors is shown.

In a storage tank 31, synthetic sewage is stored and supplied to an aeration tank 33 at a constant flow rate by a pump 32. Sludge-mixed sewage 34 is led to a settling tank 35 from the aeration tank 33 by overflow, where supernatant water 37 is separated from settled sludge 36. Most of the settled activated sludge is returned to the aeration tank 33 by a return sludge pump 38 while the remaining portion of the sludge is withdrawn to the outside of the system as excess sludge 40 by an excess sludge withdrawal pump 39. Supernatant water is withdrawn to the outside of the system as treated water through a conduit 41. Aeration air 42 is supplied to the aeration tank 33 through an air diffusion conduit 43, whereby the necessary oxygen for propagation of activated sludge is given. The aeration tank 33 is tightly separated from the atmosphere, and exhaust gas 44 of the aeration tank 33 is discharged from the aeration tank 33 to the outside of the system through an exhaust gas discharge conduit 45, and a portion of the exhaust gas is dried through a conduit 46 filled with phosphorus pentaoxide and then subjected to measurement of a concentration of $N_2O$ by a highly sensitive infrared gas analyzer 47.

A test was conducted under conditions shown in Table 1, which were imitated according to the ordinary municipal sewage standard and the operating conditions of the actual aeration tank, and relationships between the $N_2O$ formation rate in the exhaust gas and other factors were investigated. The term "$N_2O$ formation rate" used herein can be obtained as a product of a concentration of $N_2O$ in the exhaust gas by an aeration air flow rate.

TABLE 1

| Sewage substrate | Glucose (ppm) | 50, 100, 150, 200 |
|---|---|---|
| | peptone (ppm) | 40, |
| | monopotassium phosphate (ppm) | 20 |
| | ammonium sulfate (ppm) | 25, 17, 8.5 |
| | inorganic salts (ppm) | 25 |
| | total nitrogen concentration (ppm) | 30, 20, 15 |
| Influent sewage flow rate (l/hr) | | 2.3 |
| Organic load (mg/g — sludge · hr) | | 8.3, 12.8, 17.4, 22 |
| Sludge concentration (ppm) | | 900–1200 |
| Return sludge flow rate (l/hr) | | 2 |
| Aeration air flow rate (l/hr) | | 120 |
| Dissolved oxygen (ppm) | | 2.5 or more |
| Aeration tank capacity (l) | | 25 |

Figure 4:
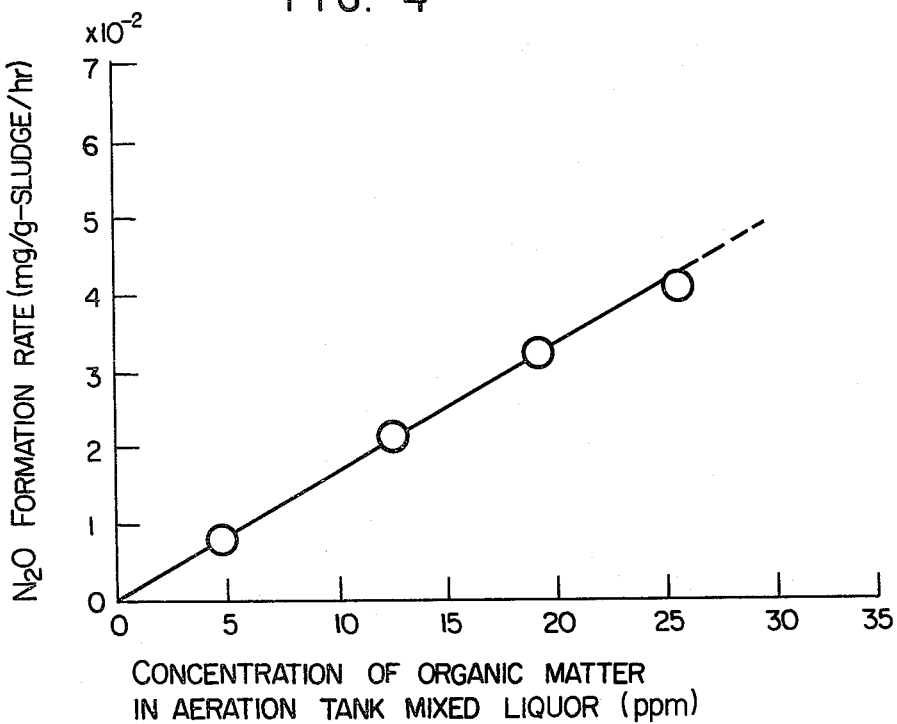
FIG. 4 is a diagram showing one example of characteristics in relationships between the concentration of organic matter and the $N_2O$ formation rate.

In FIG. 4, results of actual measurements of relationships between the $N_2O$ formation rate per unit sludge weight and the concentration of organic matter in the mixed liquor in the aeration tank, when the organic load is changed, while keeping the nitrogen concentration in the influent sewage constant are shown. As is evident from FIG. 4, the $N_2O$ formation rate is in a linear relation to the concentration of organic matter in the mixed liquor in the aeration tank. Thus, so far as the $N_2O$ concentration of the exhaust gas is known, the $N_2O$ formation rate per unit sludge weight can be calculated from the air flow rate and the sludge concentration, and the concentration of organic matter in the mixed liquor in the aeration tank can be indirectly obtained therefrom.

Explanation will be made below as to how the organic matter takes part in the $N_2O$ formation. The following formula shows a route of the well known action of activated sludge upon nitrogen compounds.

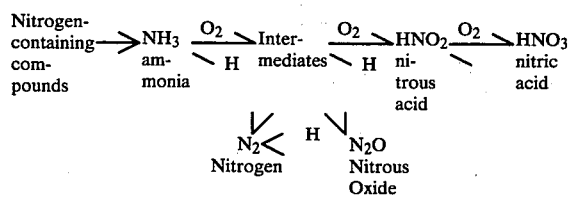

In the formula, full lines represent oxidation, dotted line reduction, and H a proton donor.

According to said mechanism, $N_2O$ is formed by oxidation and reduction of the nitrogen compounds in the influent sewage. In the reduction process, the proton donor (the organic matter in the aeration tank) is required, and the organic matter in the mixed liquor takes part in the formation of $N_2O$.

Figure 5:
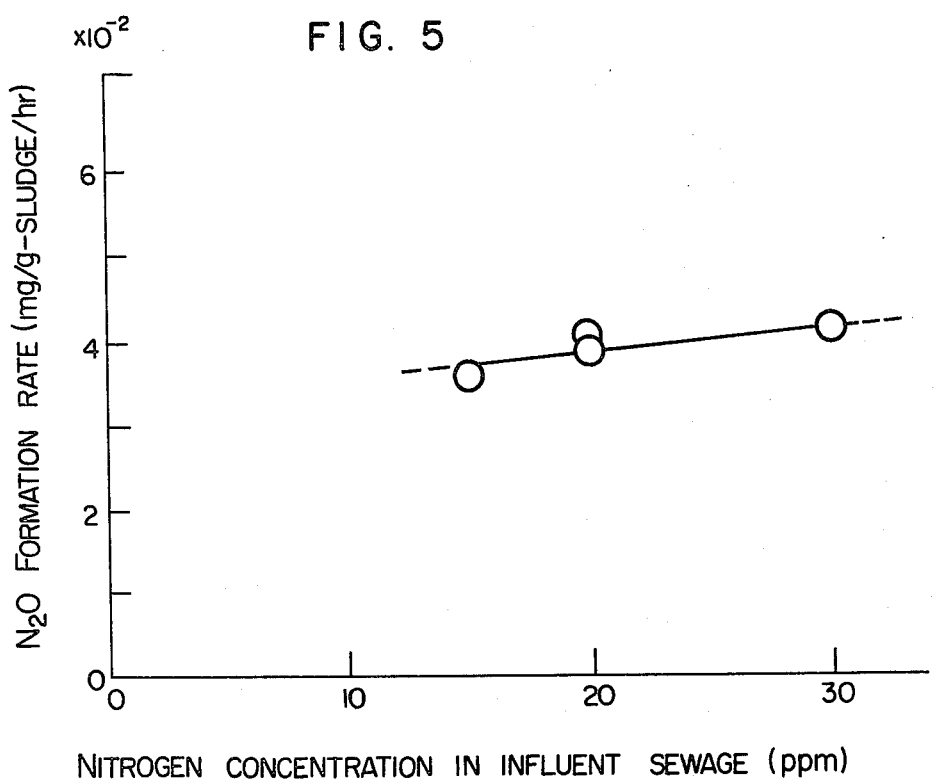
FIG. 5 is a diagram showing one example of characteristics in relationships between the nitrogen concentration in influent sewage and the $N_2O$ formation rate.

In FIG. 5, relationships between the $N_2O$ formation rate per unit sludge weight and the nitrogen load where the nitrogen load is changed while keeping the concentration of organic matter in the influent sewage constant are shown. The $N_2O$ formation rate tends to increase with increasing nitrogen load, but this tendency is small and neglible in the nitrogen concentration range of 15 ppm to 25 ppm of the ordinary sewage. That is, $N_2O$ is not influenced by the nitrogen concentration of the influent sewage.

Figure 6:
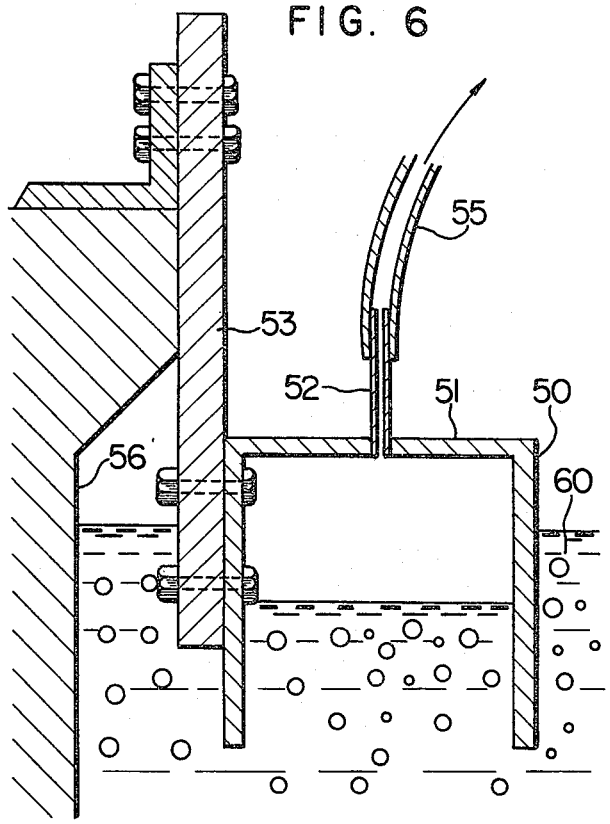
FIG. 6 is a schematic view of the structure of an exhaust gas sampling cylinder.

In FIG. 6, an example of an exhaust gas sampling cylinder 50 is shown. The sampling cylinder 50 is a cylinder with one closed end 51 and is provided with an exhaust gas pipe 52 at the center of the closed end 51. The sampling cylinder 50 is fixed by a support rod 53 so that the open end can cover a portion of the surface of the mixed liquor 60 in the aeration tank. The exhaust gas in the sampling cylinder 50 is led to an exhaust gas conduit 55 through the exhaust gas pipe 52. The support rod 53 may be fixed to a side wall 56 of the aeration tank.

On the other hand, tests of $CO_2$ was conducted by changing the concentration of synthetic sewage to three stages and also by changing the air flow rate to 5 stages as shown in the following Table 2.

TABLE 2

| Preparation of synthetic sewage | Equal weights of glucose, peptone, monopotassium phosphate were mixed together, and diluted with tap water |
|---|---|
| COD concentration of synthetic sewage (ppm) | 3 stages (182, 140, 92) |
| Aeration air flow rate (l/min) | 5 stages (2, 3, 4, 5, 6) |
| Aeration tank temperature (°C.) | 21–28 |

Figure 7:
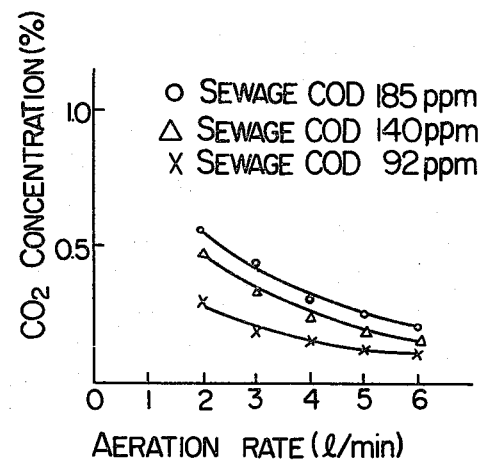
FIG. 7 is a diagram showing one example of characteristics in relationships between the air flow rate to an aeration tank and the $CO_2$ concentration.
Figure 8:
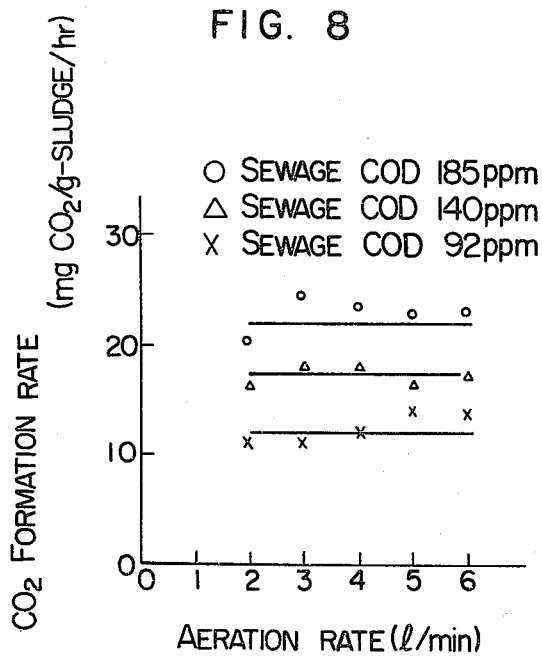
FIG. 8 is a diagram showing one example of characteristics in relationships between the air flow rate using COD of influent sewage as parameter and the $CO_2$ formation rate per unit weight of sludge.
Figure 9:
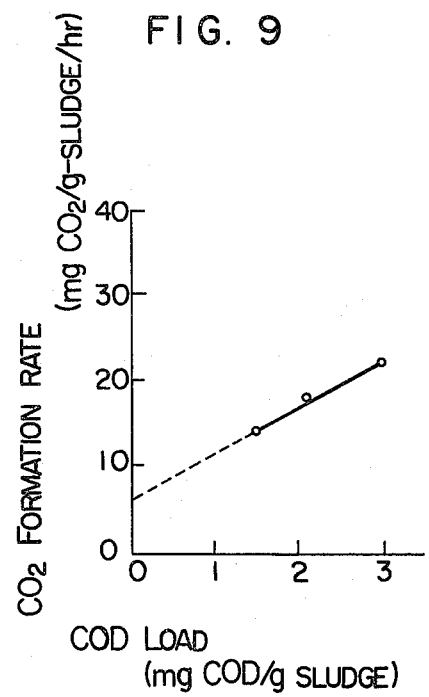
FIG. 9 is a diagram showing one example of characteristics in relationships between the COD load and the $CO_2$ formation rate per unit weight of sludge.

In the test results, relationships between the $CO_2$ concentration of the exhaust gas from the aeration tank and the aeration air flow rate are shown in FIG. 7, and relationships between the $CO_2$ formation rate per unit sludge weight and the air flow rate are shown in FIG. 8. That is, the $CO_2$ formation rate per unit sludge weight is independent of the air flow rate, but depends upon the COD concentration of crude sewage. Furthermore, relationships between the $CO_2$ formation rate and the COD load (COD supplied per unit sludge weight) are shown in FIG. 9, where a substantially linear relation is established.

That is, a simple correspondence exists between the $CO_2$ formation rate per unit sludge weight and the COD load, and this means that an organic load can be estimated without measuring the concentration of organic matter in the aeration tank by a water quality analyzer. In other words, the organic load can be controlled by estimating an organic load from a $CO_2$ concentration of the exhaust gas, and controlling a return sludge flow rate.

The similar procedure is also applicable to the case of $N_2O$ (see FIG. 4). That is, the organic load can be controlled by estimating a concentration of organic matter from an NSO concentration of the exhaust gas, and controlling a return sludge flow rate. As described above, the present invention is characterized by estimating an organic load from a $CO_2$ or $N_2O$ concentration of an exhaust gas from an aeration tank, and controlling an operating state of the aeration tank.

In the following description, control of air flow rate is explained only in the case of air, but any gas can be naturally used, so far as the gas contains oxygen.

Embodiments of the present invention will be described in detail below.

Figure 10:
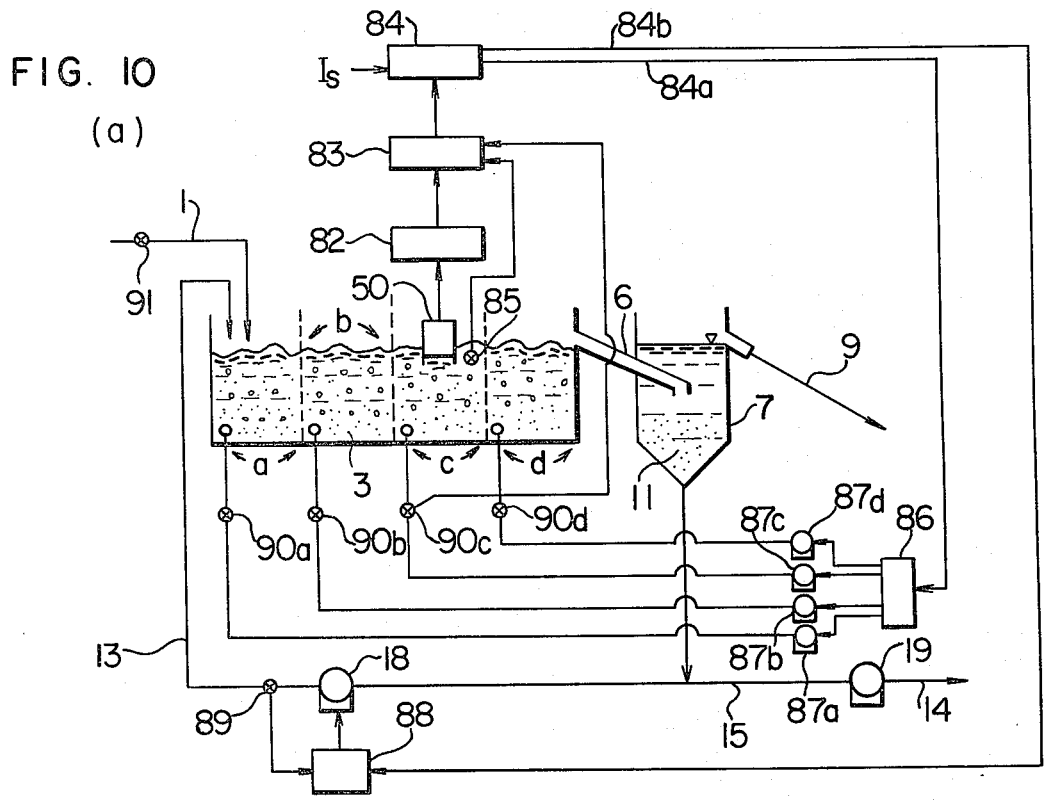
FIGS. 10 (a) and (b) are schematic diagrams according to one embodiment of the present invention.

In FIG. 10, one embodiment of the present invention is shown, where FIG. 10 (a) illustrates a flow diagram for carrying out the present invention. An exhaust gas is sampled from an aeration tank 3 by a gas sampler 50 provided at any position in the aeration tank 3, and a $N_2O$ or $CO_2$ concentration of the exhaust gas is measured by an infrared gas analyzer 82. At the same time, an aeration air flow rate and a sludge concentration at the exhaust gas sampling point are measured by an air flow rate meter 90c and a sludge concentration meter 85, respectively. An $N_2O$ or COD formation rate is calculated by a computing element 83 from the measured $N_2O$ or $CO_2$ concentration, air flow rate and sludge concentration, and a concentration of organic matter in the mixed liquor in the aeration tank is indirectly estimated therefrom, and a gas flow rate or a return sludge flow rate is controlled so that the concentration of organic matter can be removed in the predetermined range. Numerals 87a–d designate blowers, 84 a controller, 1 influent sewage, 7 a sedimentation tank, 9 treated water 13 return sludge, and 14 excess sludge. Numeral 86 designates a blower selective control circuit, which selects and controls any of blowers 87a–d by a signal 84a. In controlling a specific zone, though not specially partitioned in this case, for example, any of zones a–d shown in FIG. 10 (a), the corresponding blower is selectively controlled. Generally, gas blowing rates 90a–90d are set in specific proportions, and the entire blowers (in this case four blowers 87a–d) are controlled while maintaining said specific proportions. Output signal 84b from the controller 84 is a value for calculating an organic load in the aeration tank from the concentration of organic matter, which has been converted to an adjusted target value of the return sludge flow rate, and a return sludge pump controller 88 calculates a deviation signal from the value of return sludge flow rate detector 89 and controls the return sludge pump 18.

Signals 84a and 84b can be obtained by calculation, but generally can be obtained according to a memory table indexing system by providing a memory device in the controller 84, thereby memorizing the relationships of FIG. 4 or FIG. 9, estimating a concentration of organic matter in the aeration tank by indexing and using a deviation signal from predetermined target concentration of organic matter Is in relation to the predetermined gas flow rate or return sludge flow rate. For example, a system shown in FIG. 10 (b) is available, where $m_1$ is a memory, which, for example, memorizes a conversion table from a $CO_2$ or $N_2O$ formation rate signal to a concentration of organic matter, $C_1$ is a computer for deviation from the target concentration of organic matter Is, and $m_2$ is a memory of conversion table to adjusted target values of gas flow rate and return sludge flow rate.

Figure 11:
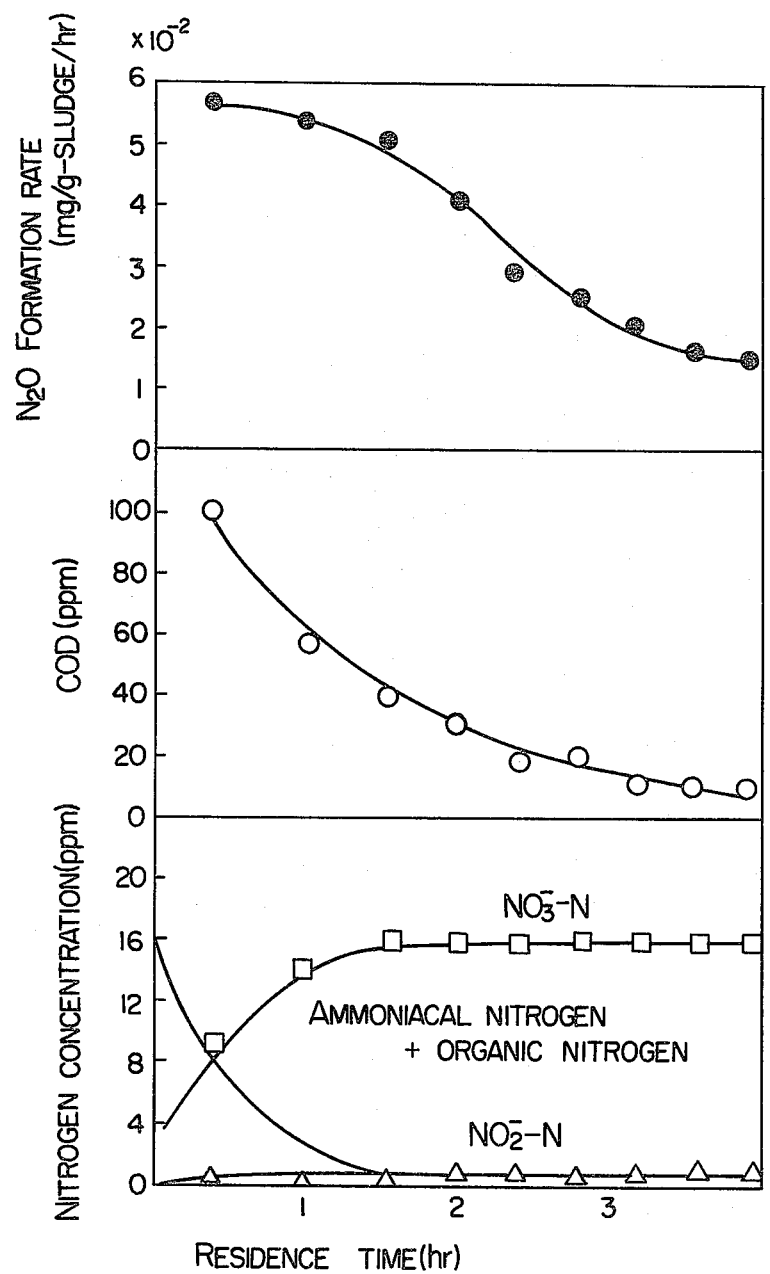
FIG. 11 is a diagram showing one example of test results.

In FIG. 11, residence time in an aeration tank is plotted on the abscissa and $N_2O$ formation rate, COD and nitrogen concentration are plotted on the ordinate. After the residence time of about one hour 30 minutes, the nitrogen component in the crude sewage is oxidized to nitrate from nitrogen-contained compound and nitrite form nitrogen-contained compound, and the $N_2O$ formation rate is decreased with decreasing concentration of organic matter in the sewage.

It is evident from FIG. 11 that the $N_2O$ formation rate is proportional to the concentration of organic matter in the sewage, and it is seen that it is preferable to provide an $N_2O$ sampling point of the exhaust gas from the aeration tank at a position at which the residence time of at least one hour 30 minutes is available, where the nitrate concentration becomes constant.

Figure 12:
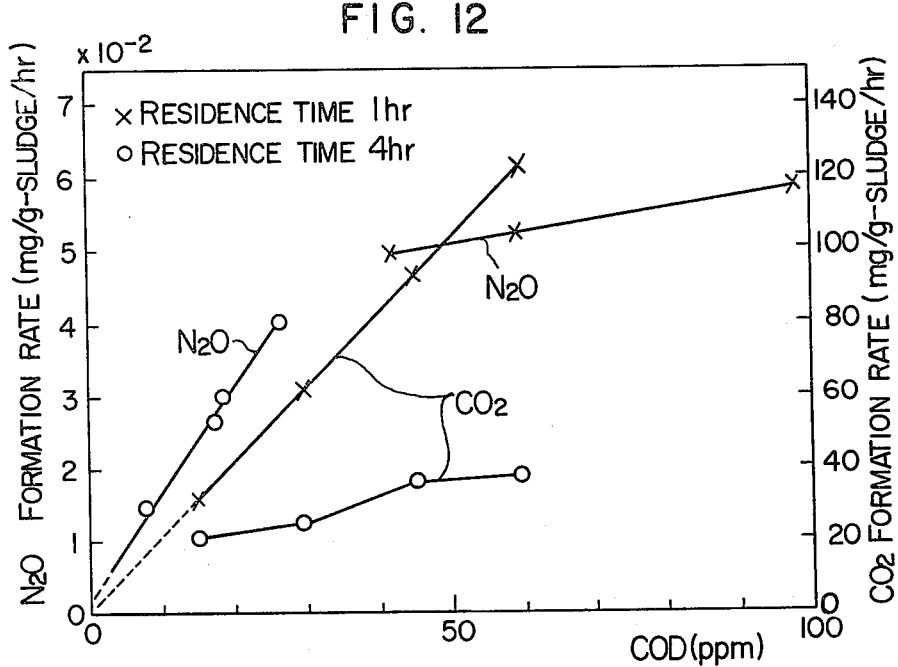
FIG. 12 is a diagram showing characteristics in relationships between COD and the $N_2O$ and $CO_2$ formation rates.
Figure 13:
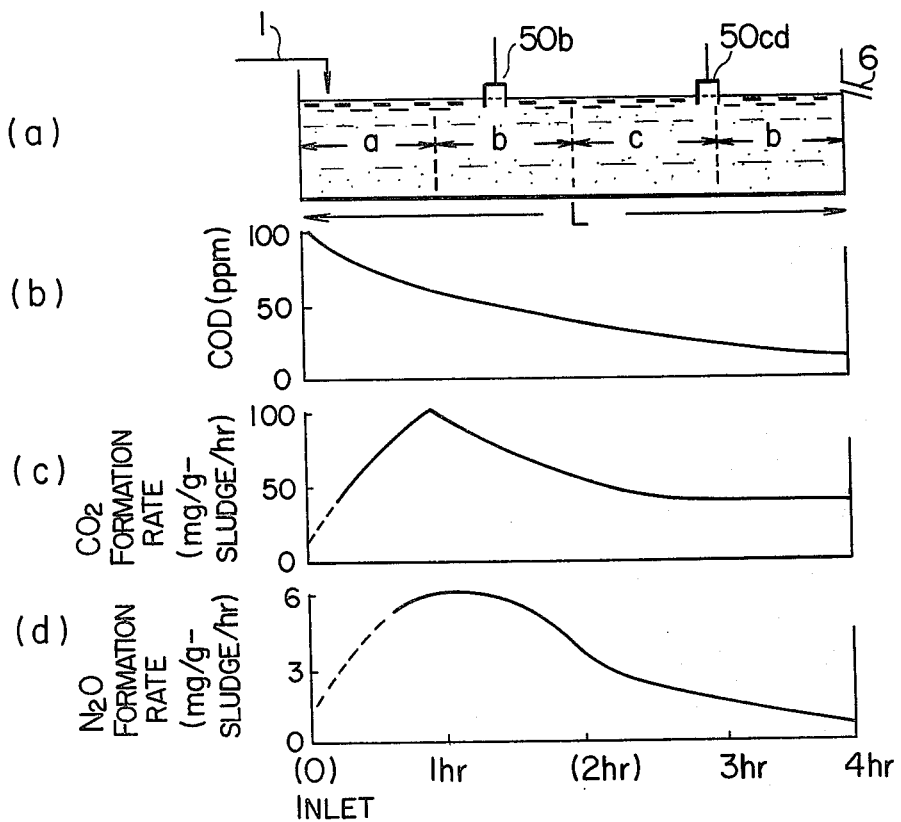
FIG. 13 is a diagram showing characteristics in relationships between the residence time and COD, and $CO_2$ and $N_2O$ formation rates.

The foregoing is the case of $N_2O$, and COD detection characteristics of $N_2O$ and $CO_2$ by the residence time are shown in FIG. 12, where the $N_2O$ and $CO_2$ formation rates are given for the residence time of one hour and 4 hours. It is seen from FIG. 12 that in the case of the residence time of one hour, $CO_2$ has a better COD detection sensitivity, whereas in the case of the residence time of 4 hours, $N_2O$ has a better COD detection sensitivity. These relationships are illustrated in FIG. 13, referring to the inlet and the outlet of an aeration tank. FIG. 13 (a) is a schematic view of an aeration tank having a length "L" between the inlet and the outlet. FIG. 13 (b) shows a COD value along the longitudinal direction of the aeration tank, and it is seen therefrom that COD is high near the inlet for the influent sewage, whereas COD is low near the outlet. FIGS. 13 (a) and (d) show distribution of $CO_2$ and $N_2O$ formation rates in such aeration tank. It is seen therefrom that both $CO_2$ and $N_2O$ cannot serve as the index for COD within the zone of the residence time of less than one hour (zone a), but $CO_2$ has a good correlation with COD in the zone b, whereas $N_2O$ has a good correlation with COD in the zones c and d. That is, it can be said that in the mixing zones b–d excluding the zone a serving as the inlet for influent sewage, measurement of $CO_2$ concentration in the former half and that of $N_2O$ concentration in the latter half can serve as a suitable index for COD. Thus, an exhaust gas sampling cylinder 50b in the zone b shown in FIG. 13 (a) is directed to the analysis of $CO_2$, and a sampling cylinder 50cd provided at the boundary between the zones c and d is directed to the analysis of $N_2O$. Appropriate control of a concentration of organic matter can be carried out by controlling the gas flow rate or return sludge flow rate to the aeration tank on the basis of the measured $CO_2$ and $N_2O$ concentrations.

It is seen from the relationships shown in FIGS. 13 (b) and (d) that in the case of $N_2O$, no correlation with COD is lost at the position near the outlet of the aeration tank even if COD is smaller. The continued decrease in COD at the position near the outlet of the aeration tank means that the assimilation action of the microorganisms upon the organic matter is in progress in the mixing zone, and when the mixed liquor in such a state is led to the sedimentation tank, an improvement of quality of effluent water cannot be attained, even though the concentration and separation of the sludge can be carried out.

Figure 14:
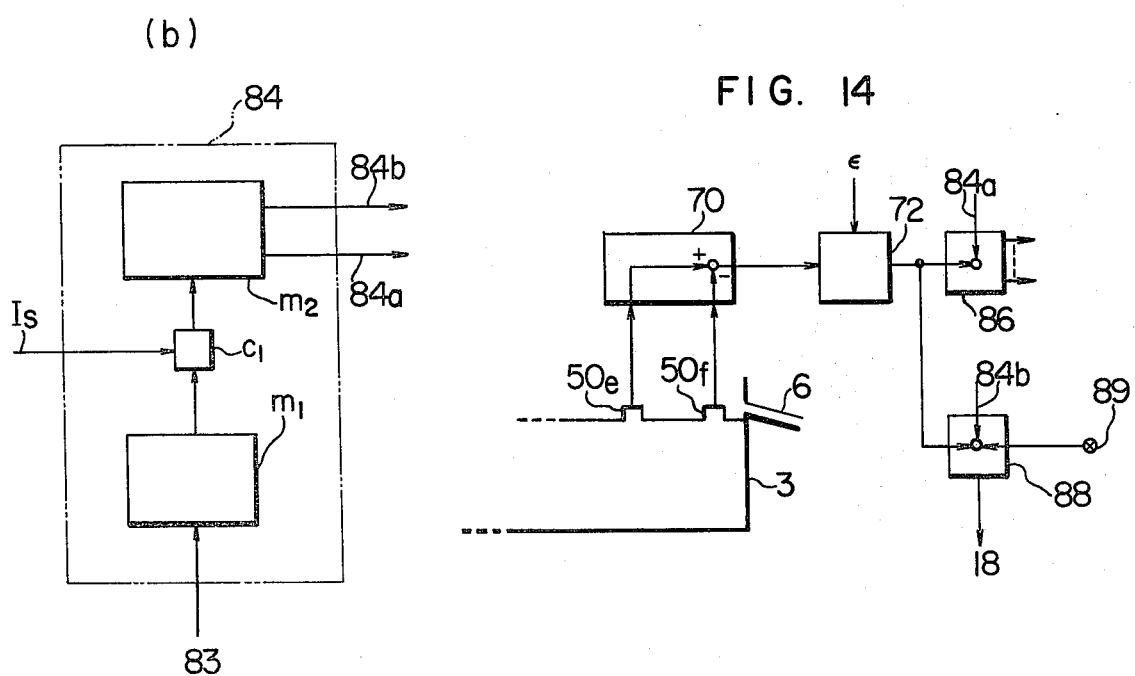
FIGS. 14, 15 and 17 are schematic diagrams according to other embodiments of the present invention.

Thus, in order to improve the quality of effluent water from the sedimentation tank, it is necessary to control the COD reduction ratio at the position near the outlet of an aeration tank to less than the predetermined value. FIG. 14 shows one embodiment of such a case. At first, $N_2O$ is detected at least at two arbitrary points near the outlet of the aeration tank. A deviation between the $N_2O$ concentration detected by an exhaust gas sampling cylinder 50e and the $N_2O$ concentration detected by 50f is calculated by a deviation computer 70 and the deviation signal $\delta$ is compared with the predetermined small value $\epsilon$ in a comparator 72. The case of $\delta < \epsilon$ means that the assimilating action of microorganisms is fully carried out in the mixing zone, and it is judged in this case that the gas flow rate to the aeration tank can be decreased. On the other hand, the case of $\delta < \epsilon$ means that the assimilating action is still going on in the mixing zone, and thus the gas flow rate to the aeration tank must be increased to promote the assimilating action. That is, this embodiment is characterized by controlling a gas flow rate not only by the absolute value of $H_2O$ at the position near the outlet of an aeration tank, but also by a rate of change in $N_2O$ concentration, thereby carrying out the assimilating action satisfactorily in the aeration tank. The deviation signal $(\delta - \epsilon)$ in the comparator 72 is added to an adjustment control signal to the blower selective control circuit 86 or the return sludge pump controller 88.

Figure 15:
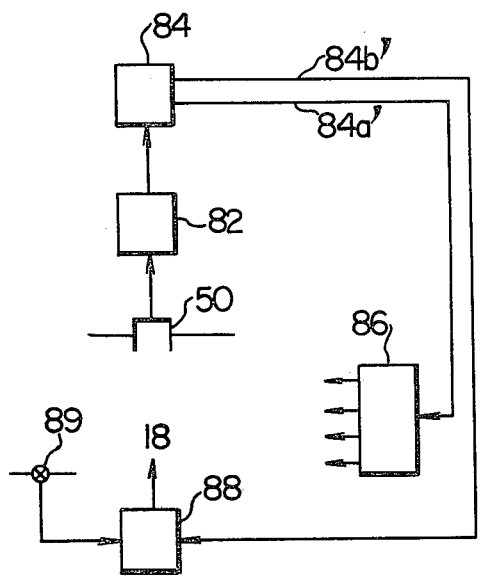

In the computer 83 of FIG. 10, the $N_2O$ formation rate or the $CO_2$ formation rate is calculated from the air flow rate and the sludge concentration, and is fed as a control signal to the blower selective control circuit 86 for a return sludge pump controller 88, but when the sludge control is separately carried out by a minor loop, the control can be directly carried out by the $H_2O$ concentration signal and $CO_2$ concentration signal obtained by the infrared gas analyzer 82. One embodiment of such a case is shown in FIG. 15, where the signals are directly fed to a controller 84' from the infrared gas analyzer 82, and the blower or return sludge pump is controlled by signals 84'a and 84'b.

In FIG. 10, the gas blowing rate is controlled by providing separate blowers correspondingly to the zones a-d, but blowing by a single blower and branching a blower line into a plurality of lines in an aeration tank (for example, as shown by 4 in FIG. 1) will never spoil the effect of the present invention.

Figure 17:
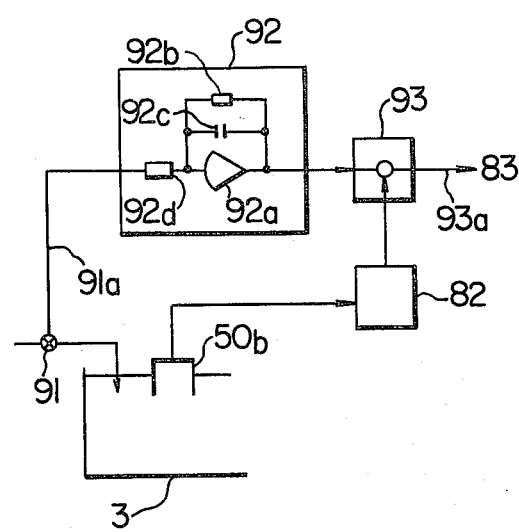
Figure 16:
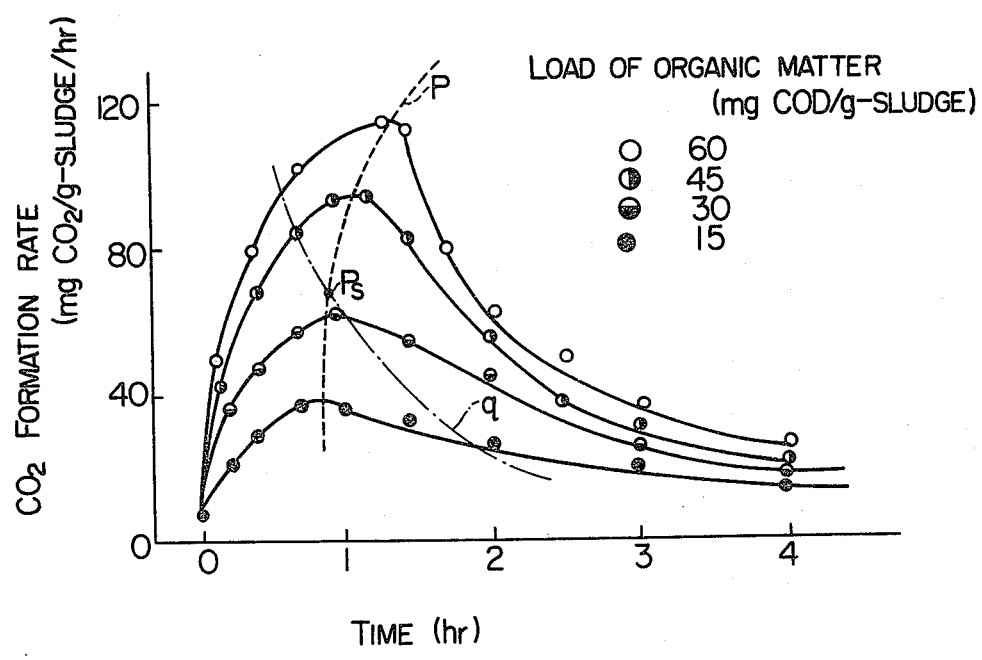
FIG. 16 is a diagram showing characteristics in relationships between the change in flow rate and the $CO_2$ formation rate.

In the case of measuring the $CO_2$ formation rate, the detector is provided at the position near the inlet for the influent sewage, and it has been experimentally confirmed that the measurement is greatly influenced by the influent sewage flow rate. The results are shown in FIG. 16, where the organic load is changed to four stages, and a dotted line is plotted on the peaks of $CO_2$ formation rate. It is seen therefrom that peak point is shifted towards the right side, that is, increasing time direction, with increasing organic load,. On the other hand, when the sampling point is fixed, and points of $CO_2$ concentration detected at the fixed sampling point are plotted, a line q (alternate long and short dash line) is obtained. Generally, the detector is fixed at the position showing the $CO_2$ peak value, but when the influent sewage flow rate is changed, the peak value of $CO_2$ formation rate cannot be obtained without making adjustment of the detected value. Thus, when the influent sewage flow rate is changed, adjustment should be made in view of the time lag until the influence reaches the detector position. FIG. 17 shows one embodiment of such a case. Influent sewage flow rate signal 91a from an influent sewage flow rate detector 91 is fed to an adder 93 through a time lag circuit 92 (in this case, analog primary lag circuit, i.e., an analog first order lag circuit) to adjust or compensate the detected $CO_2$ concentration signal. Time constant of the time lag is set on the basis of the characteristics of a given aeration tank. Numerals 92a and 92b are resistors, 92c a condenser, and 92a an operational amplifier. The time constant of the primary lag circuit can be set, as desired, by the value of condenser 92c and the value of resistor 92b. The thus adjusted or compensated signal 93a can show a peak value even if the sampling position for analyzing an exhaust gas is fixed.

FIG. 17 shows the case of $CO_2$ detector 50b, but the same thing is also applicable to the case of $N_2O$ detector 50cd, with such differences in the time constant from the position to the position at which the respective detectors are set, and the correction gain set by ratio of values of resistors 92b and 92d, and there is no substantial difference therebetween.

An application of the present invention to the case where a sludge-storing zone is provided in an aeration tank will be described below. FIG. 18 (a) shows an aeration tank with a sludge storing zone, where the zone a of the aeration tank shown in FIG. 10 is used as a storing zone for sludge 13a and the sludge is stored in the zone a in advance, and the necessary sludge is supplied to the mixing zone through a plurality of openings on a partition plate 94.

One example of the function will be described below. Sewage is supplied to the aeration tank 3 through a valve 95. The $CO_2$ concentration 100 detected by the detector 50b is compared with the predetermined value 100s in a comparator 99, and when the detected $CO_2$ concentration 100 is larger than the predetermined value 100s, a change-over switch 97 switches contact 91 to contact a₂ by comparator output signal 99a. The valve 95 is fully closed, and the influent sewage is supplied to the storing zone through a valve 96 to discharge the sludge 13a in the storing zone to the mixing zone by the influent sewage. The discharge of the sludge is carried out by the influent sewage, and thus the present embodiment is characterized in that the sludge in the amount substantially corresponding to the amount of the influent sewage, can be supplied, and a response speed is higher than that by supplying the return sludge 13 by the return sludge pump, and this system is called "dynamic" sludge-storing system in the aeration tank by the present inventors. Numeral 98 is a valve controller. After the valve is switched, $CO_2$ is detected and monitored by a detector 50b₂.

Characteristics of this case are shown in FIGS. 18 (b)-(d). FIG. 18 (b) shows COD, FIG. 18 (c) a $CO_2$ formation rate, and FIG. 18 (d) a $N_2O$ formation rate, where the full line represents the case of supplying the influent sewage through the valve 95 and the dotted line the case of supplying the influent sewage after switching to the valve 96, that is, through the storing zone. In FIG. 18, the switching of valve 95 to 96 is illustrated, but the set value of the degree of opening or the set value of flow rate through the respective valves can be also adjusted. An embodiment of such a case is shown in FIG. 19. Numerals 116 and 118 are influent sewage flow rate detectors to the storing zone and the mixing zone, respectively. Fa and Fb are target values of the respective flow rates. Adjusted target flow rate value Fc is calculated in a computer 101 from the detected $CO_2$ concentration. The value Fc can be sometimes determined from experiences, or a computer capable of outputting Fc as a constant value only when the $CO_2$ concentration is higher than the predetermined value can be used. In an adder 108, the target value Fb is adjusted, and the valve 95 is controlled by a deviation signal between the adjusted target value F'b and the flow rate from the flow rate detector 118, for example, by a proportional plus integral controller 102. The same thing is also applicable to the storing zone.

Adjustment of target value Fa is carried out in an adder 114 by signal Fc·K obtained by multiplying the signal Fc by K set in a coefficient multiplier 116. The valve 96 is controlled by a controller 104 similar to 102 by a deviation signal ΔFa so as to meet the adjusted target signal Fa'. The coefficient K of the coefficient multiplier 106 is set in advance. The value of coefficient K can be stagewise changed by the detected $CO_2$ concentration, though its detail is not shown in FIG. 19. In FIG. 19, K is switched by a coefficient selective circuit 120 shown by the dotted line.

The effect of the case where control of the air flow rate is carried out by using $N_2O$ as an index for reduction of organic matter in aeration tank.

Results of DO control when the influent sewage rate to an aeration tank is changed according to the variation in the ordinary municipal sewage are shown in FIG. 20.

FIG. 20 (a) shows variation in influent sewage rate.

FIG. 20 (b) shows concentration of organic matter at N$_2$O reduction point.

FIG. 20 (c) shows comparison of the case of the control of the air flow rate by detecting N$_2$O in the exhaust gas as an index for reduction of organic matter in aeration tank according to the present invention and the case of air flow rate by a DO meter under said conditions.

Tests were carried out by automatic analysis of N$_2$O concentration in the exhaust gas and automatic determination of sludge concentration, estimating the concentration of organic matter in the sewage from the N$_2$O formation rate, and manual control of gas flow rate so that the concentration of organic matter can approach the target value. In the case of DO control, the percent removal of organic matter in the treated water is 87–94%, whereas in the case of controlling the air flow rate so that the estimated concentration of organic matter in the mixed liquor in the intermediate zone of the aeration tank can be within the range of 20–30 ppm, the percent removal of organic matter in the treated water is 92–95%. It is seen therefrom that the present invention is effective.

In the present invention, the concentration of organic matter in mixed liquor can be determined with good precision when variation in the nitrogen concentration of sewage is small. However, even if the variation in the nitrogen concentration in sewage is large, control of decreasing the concentration of organic water in the sewage can be carried out on the basis of the N$_2$O formation rate. That is, the N$_2$O formation rate is determined at least at two sampling points in the aeration tank. Since variation in nitrogen concentration in the sewage with time is small, it can be presumed that the N$_2$O formation rate at least at two sampling points is proportional to the concentration of organic matter at these sampling points. Thus, the gas blowing rate or sludge concentration must be controlled so that a difference in the N$_2$O formation rate at these sampling points can be smaller.

DO and N$_2$O concentration are in the relationships as shown in FIG. 21 (a), where the N$_2$O concentration is higher with small DO content. This can be preferably utilized as a DO alarm signal generation. For example, as shown in FIG. 21 (b), comparison of N$_2$O concentration signal with DO lower limit value D$_{set}$ is made in a comparator COMP, and an alarm signal is made to generate in the case of N$_2$O > D$_{set}$. In this manner, a simple DO alarm circuit can be made available.

What is claimed is:

1. A process for controlling an aeration tank in an apparatus for sewage treatment by activated sludge which apparatus includes an aeration tank for stirring and mixing inflow sewage with activated sludge and a gas containing oxygen, a sedimentation tank for settling a mixed liquor from the aeration tank, thereby concentrating and separating sludges converted by assimilating action of microorganisms upon organic matter in the sewage, a gas blowing means for supplying the gas containing oxygen into the aeration tank, and a sludge return means for returning the sludge concentrated and separated in the sedimentation tank to the aeration tank, said process comprising the following steps:
   (a) a step of measuring a concentration of carbon dioxide of an effluent gas from the aeration tank at the sewage inflow side of the aeration tank,
   (b) a step of measuring a concentration of nitrous oxide of an effluent gas from the aeration tank at the sewage outflow side of the aeration tank, and
   (c) a step of controlling the aeration rate at the sewage inflow side corresponding to the side of measuring the concentration of carbon dioxide from the aeration tank by the gas blowing means, thereby making the measured concentration of carbon dioxide equal to a predetermined value and
   (d) a step of controlling the aeration rate at the sewage outflow side corresponding to the side of measuring the concentration of nitrous oxide from the aeration tank by the gas blowing means, thereby making the measured concentration of nitrous oxide equal to a predetermined value.

2. The process according to claim 1, wherein the steps (c) and (d) further include controlling the return sludge rate by the sludge return means, thereby making a concentration of organic matter computed from the measured nitrous oxide concentration equal to a predetermined value.

3. The process according to claim 1, wherein the step (d) includes the following steps:
   (i) a step of measuring nitrous oxide concentrations at two different points at the sewage downstream side of the aeration tank along the sewage outflow direction and
   (ii) a step of controlling the aeration rate at the sewage downstream side according to the difference between the measured nitrous oxide concentrations at the two points.

4. The process according to claim 3, wherein the step (ii) comprises:
   (a) a step of comparing a signal of difference between the values measured at the two points by the predetermined value of the nitrous oxide concentration,
   (b) a step of increasing the aeration rate when the difference between the values measured at the two points is more than the predetermined value, and
   (c) a step of decreasing the aeration rate when the difference between the values measured at the two points is less than the predetermined value.

5. A process for controlling an aeration tank in an apparatus for sewage treatment by activated sludge which apparatus includes an aeration tank for stirring and mixing inflow sewage with activated sludge and air, a sedimentation tank for settling a mixed liquor from the aeration tank, thereby concentrating and separating sludges converted by assimilating action of microorganisms upon organic matter in the sewage, a gas flowing means for supplying a gas containing oxygen into the aeration tank, a sludge return means for returning the sludge concentrated and separated in the sedimentation tank to the aeration tank, and a carbon dioxide detecting means for detecting a carbon dioxide component in an effluent gas from the aeration tank, said process comprising the following steps under control of aeration rate and sludge return rate:
   (a) a step of measuring a concentration of carbon dioxide of the effluent gas from the aeration tank at the upstream side from the center in the aeration tank,
   (b) a step of measuring a sewage inflow rate to the aeration tank,
   (c) a step of imputting the sewage inflow rate signal measured in step (b) into a time lag circuit,
   (d) a step of adding an output signal from the time lag circuit to the signal of the measured carbon dioxide concentration, thereby adjusting the signal of measured carbon dioxide concentration, (e) a step of estimating a concentration of organic matter in the aeration tank from the adjusted signal of the carbon dioxide concentration, (f) a step of controlling the return sludge rate by the sludge return means in accordance with the deviation of the predetermined value from the estimated value obtained in the step (e) when a concentration of organic matter is predetermined as a control target value of the aeration tank, and (g) a step of computing an aeration rate to the aeration tank with a gas blowing means in accordance with the deviation of the predetermined value from the measured carbon dioxide concentration obtained in the step (a), when a signal of carbon dioxide concentration is predetermined as a controlled target value of the aeration tank.

6. The process according to claim 5, wherein the aeration tank comprises a sludge-retaining zone and a successive mixing zone, and process further comprising the following steps:

(i) a step of continuously introducing inflow sewage to the mixing zone and detecting a concentration of carbon dioxide of the effluent gas from the mixing zone, and (ii) a step of switching the introduction of the inflow sewage to that to the sludge-retaining zone when the detected concentration of carbon dioxide reaches the predetermined value.

7. The process according to claim 5, wherein the aeration tanks comprises a sludge-retaining zone and a successive mixing zone and said process further comprising the following steps:

(i) a step of introducing the inflow sewage to both of the sludge-retaining zone and the mixing zone, and (ii) a step of adjusting the predetermined value of sewage inflow rate to both zones by a concentration of carbon dioxide in the effluent gas from the mixing zone.

* * * * *